United States Patent [19]

Athey et al.

[11] 4,299,115
[45] Nov. 10, 1981

[54] METHOD AND APPARATUS FOR ANALYSIS OF MEAT PRODUCTS

[75] Inventors: Stuart E. Athey; Dick P. McCord, both of Troy, Ohio

[73] Assignee: Hobart Corporation, Troy, Ohio

[21] Appl. No.: 80,802

[22] Filed: Oct. 1, 1979

[51] Int. Cl.³ .................... G01N 5/04; G01N 25/00
[52] U.S. Cl. ........................ 73/15 B; 219/10.55 R; 364/567
[58] Field of Search ................ 73/15 B, 76; 364/567

[56] References Cited

U.S. PATENT DOCUMENTS

| | | | |
|---|---|---|---|
| 3,183,710 | 5/1965 | Spang | 73/76 |
| 3,673,852 | 7/1972 | Davis | 73/15.4 |
| 3,813,918 | 6/1974 | Moe | 73/15 B |
| 3,890,825 | 6/1975 | Davis | 73/15 B |
| 3,902,354 | 9/1975 | Harlan et al. | 73/15 B |
| 3,909,598 | 9/1975 | Collins et al. | 364/567 |
| 3,916,670 | 11/1975 | Davis et al. | 73/15 B |

Primary Examiner—Daniel M. Yasich
Attorney, Agent, or Firm—Biebel, French & Nauman

[57] ABSTRACT

Rapid and accurate determination of the fat, moisture, and protein content of meat products such as beef or the like is obtained by exposing a sample to microwave energy for a period of time sufficient to achieve a relatively constant chemical analysis in the residue. During heating on a weighing device, a substantial portion of the moisture in the sample is vaporized and a substantial portion of the fat is melted and collected in a separate container which is maintained below the sample but off of the weighing device. By monitoring the time rate of change of weight loss in the sample until it reaches a predetermined value and terminating cooking, a relatively constant chemical analysis of the residue is achieved. Collection of rendered fat off of the weighing device avoids erratic fluctuations in weight readings caused by spattering, dripping, and explosions of the melted fat in the collection container.

13 Claims, 5 Drawing Figures

METHOD AND APPARATUS FOR ANALYSIS OF MEAT PRODUCTS

CROSS REFERENCE TO RELATED APPLICATIONS

This application is related to U.S. application Ser. No. 080,803, filed Oct. 1, 1979, entitled "Magnetic Coupling for a Weighing Balance Assembly", and is also related to U.S. application Ser. No. 080,841, filed Oct. 1, 1979, entitled "Use of Acid as an Analysis Aid in Salted Meat Samples," both applications being assigned to the assignee of this application.

BACKGROUND OF THE INVENTION

This invention relates to a method and apparatus for the analysis of food material, such as meat products, and more particularly to an improved process for quick and accurate determination of the percentage of fat, moisture, and protein in products such as beef, pork, combinations thereof, and the like. Related methods are disclosed in U.S. Pat. Nos. 3,673,852, 3,890,825, and 3,916,670 to the assignee of this application.

In meat products which are intended for human consumption and which are comminuted during processing, the accurate control of fat and/or moisture content arises. Typical of such meat products are ground beef, pork, veal, lamb, pork sausage and meat products such as bologna, weiners, and liverwurst. The usual procedure is to feed chunk meat into a grinder and then into a mixer to bring about intermixing of the meat product ingredients. It is after the mixing operation that the composition is checked and adjustments made in the fat to lean ratio and/or moisture content. Following this, the meat is then ground a second time or further processed by mixing and blending with seasonings and the like and checked again for compositional content.

This invention is primarily directed to the analysis of ground meat, the composition of which may vary considerably depending on the grade. Ground fresh meat products may contain between 10 and 30 percent fat. Control of the fat content is critical to meeting both regulatory and profit objectives. In cured sausage products such as weiners and bologna, control of both fat and added moisture content is required in order to meet regulatory limits. This invention helps the user to maintain control of the aforementioned chemical components of meat products by providing accurate, timely analysis results during the formulation process.

Apart from close cost control by the processor, there is also protection of the consumer in that the amount of fat or moisture may vary in a meat product from day to day, notwithstanding the processor's good faith attempts to control these variables. In many cases of contract sales, fat content is specified and penalties imposed for exceeding the maximum amounts stated. Fat and moisture content have also been important constituents in diet control for hospitals, nursing homes, and the like. Finally, it would be advantageous, both to the processor and consumer, to have each packaged meat product labeled with the percentage of fat, moisture, and protein.

Currently, the standard determination of fat is by the "Official Methods of Analysis of the Association of Official Analytical Chemists" (AOAC) ether extraction method which takes about 8 to 24 hours for final results. The fact is that not all fats are ether extractable, while conversely, some non-fat materials are ether extractable. Accordingly, an absolute standard does not exist.

Another method which is rapid and effective is disclosed in U.S. Pat. No. 3,183,710 assigned to the assignee of this application. This latter method involves direct heating of a comminuted meat sample to melt the fat and to remove the moisture and fat in liquid form.

The method of analysis taught in U.S. Pat. No. 3,673,852, assigned to the assignee of this application, is an improvement of that method. In that patent, comminuted meat is exposed to microwave energy which vaporizes moisture in the sample and renders fat present in the sample. Use of microwave energy for this purpose enables even heating of the sample throughout without producing uneven cooking or charring of the sample. The methods and apparatus disclosed in U.S. Pat. Nos. 3,890,825 and 3,916,670, also assigned to the assignee of the present invention, represent improvements over the earlier patents. In these patents, a sample of comminuted meat is continuously monitored during cooking until the rate of weight loss of the sample decreases to a predetermined value. In this manner, reproducibility and accuracy in sample analysis is increased.

However, problems have been encountered during the monitoring of the sample. Fat rendered from the sample during cooking and collected in a beaker beneath the sample on a weighing scale repeatedly spatters and explodes. These explosions which are caused by droplets of moisture falling into the hot fat and violently boiling, induce vibrations in the weighing scale, driving weight readings through erratic fluctuations. Consequently, it becomes difficult to monitor accurately the rate of weight loss to ascertain when a predetermined value has been reached.

Additionally, the weight loss recorded during cooking represents only that loss due to moisture vaporization. For some meat samples, the moisture weight loss is relatively small so that the rate of weight loss is difficult to measure, making it more difficult to ascertain when a predetermined rate has been reached.

Accordingly, the need still exists in the art for a process and apparatus which will provide an easy and accurate analysis of the fat, moisture, and/or protein content of meat samples over a broad range of content variations.

SUMMARY OF THE INVENTION

The present invention represents a further improvement over the methods and apparatuses disclosed in U.S. Pat. Nos. 3,890,825 and 3,916,670. The present invention, as do the earlier inventions, involves exposing a sample of comminuted meat of known weight to microwave energy. By using microwave energy, water or moisture in the sample is removed directly as vapor rather than a liquid. Microwave energy effects uniform treatment of the sample at all points since heat is generated primarily by oscillation of the water and fat molecules in the sample. The heat thus produced "renders" or melts the fats present in the sample which have a melting point below 212° F., primarily lard and tallow fats having a melting point in the range of 90°–124° F. In beef, these fats are organic compounds having chain lengths of 11 to 19 carbons while in pork, the chain length is 13 to 19 carbons with pork overall containing a greater number of short chain length carbons than beef. By exposure to microwave energy, a consistent reproducible amount of these fats may be rendered without completely charring the original sample.

Where the sample is charred, protein cannot be determined accurately since some of the protein is destroyed or converted to products which are vaporized.

In the improvement of the present invention, the fat rendered from the sample during cooking is collected off of the weighing apparatus. In this manner, the prior art problems of fat exploding and spattering and causing erratic weight reading fluctuations are avoided. Additionally, since the weight loss being monitored is the combined loss due to both the vaporization of moisture and the rendering of fat, the rate of weight loss can be monitored more accurately because it is a larger value than in previous methods.

A sample holder assembly is provided which is in direct communication with a weighing balance. This assembly is adapted to support both the sample to be analyzed as well as a dish which collects rendered fat. Importantly, however, the apparatus of the present invention is also provided with a dish support assembly which is adapted to raise and lower the fat collecting dish from the sample holder assembly and, thus, bring the dish into and out of communication with the weighing balance.

During operation, the dish support assembly maintains the fat collecting dish off of the sample holder assembly. Thus, the weight loss measured due to the cooking of the sample is the combined weight loss due to vaporization of moisture and rendering of fat. After cooking has been terminated, the dish support automatically lowers the dish with collected fat back onto the sample holder assembly where it is weighed.

The solid residue weight plus the weight of the collected fat subtracted from the original sample weight provides the weight of moisture vaporized from the sample. Knowing the amount of released moisture, the amount of moisture in the sample may be predicted accurately. The amount of fat is determined by collecting the released fat, essentially free of water, and relating this collected amount to the amount of fat in the sample. Knowing the moisture and the fat, the amount of protein is calculatable in accordance with known formulae accepted in the industry.

Accordingly, it is an object of the present invention to provide an improved and repeatable process, and apparatus therefore, for analysis of food material, such as meat products, by rendering a sample using microwave energy in order to determine automatically moisture, fat, and protein and controlling the application of the microwave energy as a heat source for a period of time which is automatically terminated when essentially all moisture present in the sample has been vaporized; to provide such an apparatus wherein the fat is collected off of the weighing scale; the solid residue saved and weighed, and automatic calculation of the percentage of fat, moisture, and protein proceeds.

Other objects and advantages of the invention will be apparent from the following description, the accompanying drawings, and the appended claims.

DESCRIPTION OF THE PREFERRED EMBODIMENTS

Figure 1:
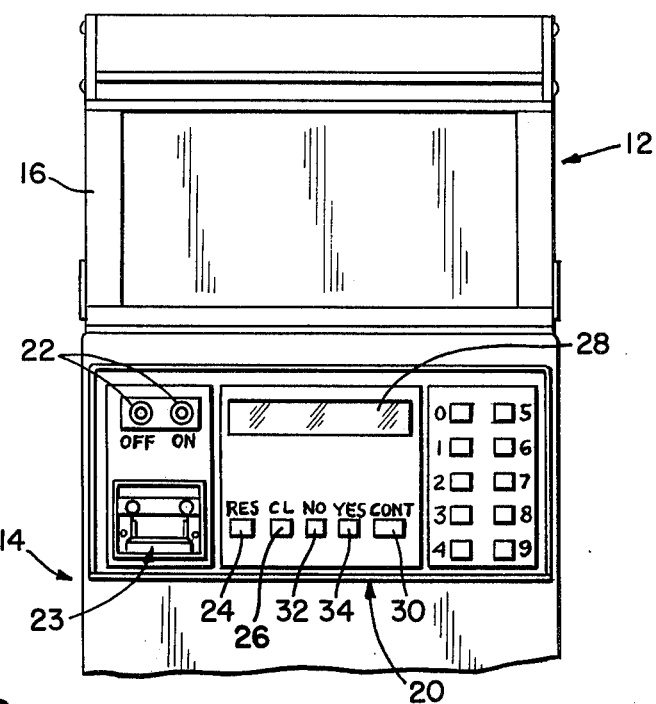
FIG. 1 is a front view of the apparatus of the present invention illustrating the control panel and microwave oven.

Analysis of food material, such as prepared samples of a meat product, is provided by rendering or "cooking" the sample to release from it moisture, primarily in the form of vapor, and fat, primarily as liquid which is collected separately from the solid residue and removed from the scale to avoid fluctuations in weight readings. By weighing the sample before and after cooking, and both with and separate from the fat, it is possible to calculate percentage of moisture and percentage of fat. Having reference to certain formulae which are well known in the meat industry, it is possible to calculate the percentage of protein in meat.

In a preferred embodiment, a comminuted meat sample is selected such that the sample weight is in the range of 70 to 80 grams. The reason for this is that the "cooking" cycle may be maintained short, e.g., 2 to $4\frac{1}{2}$ minutes. The term "cooking" in accordance with this invention is meat heated short of charring but far too well cooked to be edible in the normal sense. The use of microwave energy offers the singular advantage of generating heat throughout the sample so that it is uniformly and evenly heated. The energy from the source penetrates the sample causing oscillation of dipolar molecules, such as water, which attempt to align themselves with the polarity of the electromagnetic field, and thereby generate heat uniformly throughout the sample. The moisture, or water is vaporized and released directly as vapor. The fat molecules are excited sufficiently by the microwave energy to cause melting of the fat which then drips from the sample into a collection dish. By heating the sample short of charring, decomposition of substantial amounts of protein and fat is avoided even though some fat, moisture, and protein remains in the solid residue.

The microwave cooking thus does not remove all of the fat or moisture, but this has been found not to be critical to the determination of the percentages of these components as taught in above-mentioned U.S. Pat. Nos. 3,890,825 and 3,916,670. It has also been observed that some of the protein is removed with the moisture by decomposition and vaporization. These factors are compensated for by generating a set of constants which are a function of oven design, i.e., spacing between the microwave energy source and sample, intensity of energy source, and rate of heating and type of meat. Also a factor is the loss of fat, protein, etc., due to spattering and the vaporization of some of these components. Thus, any microwave oven will have a set of constants which can be calculated, the constants being determined easily by a simple calibration procedure, and being valid for each oven of the same design, although it may vary from one design of oven to the next. The procedure for developing such constants is discussed in the above-mentioned patents and is incorporated herein by reference. Those sampling techniques and use of multiple regression analysis have been extended to include the determination of constants for salt content and temperature in the present invention.

In general, the analysis system operates as follows. The sample holder assembly, sample holder, and sample holder cover are first weighed to establish an initial tare weight which is then stored. The fat collection dish is then lowered onto the sample holder assembly and weighed to establish a second combined tare weight which is stored. (It should be understood that whenever "collection dish" is mentioned, this also includes a dish paper and watchglass which are contained in the collection dish and help to prevent spattering.) The collection dish is then raised off of the sample holder assembly in preparation for the cooking cycle. A prepared sample of meat is then placed in the sample holder, covered, and loaded onto the sample holder assembly. After measuring and storing the weight of the sample plus the initial tare weight, the cooking cycle is initiated and continued until the rate of weight loss of the sample falls below a predetermined value. During the cooking cycle, the fat collection dish is maintained off the sample holder assembly so that the rendered fat it collects does not cause any fluctuations in weight readings. At the end of the cooking cycle, the oven is shut off and the fat containing collection dish is lowered into the sample holder assembly where the combined weight of the sample holder assembly, sample holder, sample holder cover, collection dish, sample residue, and rendered fat is recorded. The residue is then removed from the balance and the combined weight of the sample holder assembly, sample holder, sample holder cover, collection dish, and rendered fat is recorded. The moisture, fat, and protein content of the sample may then be calculated using equations which will be set forth below.

As is understood, these calculations may be automatically carried out by a computer which functions with the balance assembly in a conventional manner.

It will be apparent to those skilled in the art that the present system may be used to determine only fat content in contrast to determination of each of moisture, fat, and protein, or may be used to determine only moisture. If used to determine only protein, this can be done by determining fat and moisture but reporting only the protein results.

Various types of electronic means known to a person skilled in the art may be used to perform the weighing and calculating functions previously described. For example, a number of commercially available balances provide digital output of weight information which is easily processed in a small general purpose or special purpose computer. With such equipment the calculations are carried out manually or under the control of a set of instructions programmed into the computer.

It has been discovered that a more nearly automatic system can be provided wherein the weighing, recording, and cooking operations are performed in a fairly rapid manner, and with minimum attention which can be provided by relatively unskilled labor. This system also provides certain additional manufacturing advantages since it minimizes the need to standardize each type of oven used. The system also provies both an automatic visual readout of percentages of moisture, fat, and protein, and a printout of this information.

Figure 2:
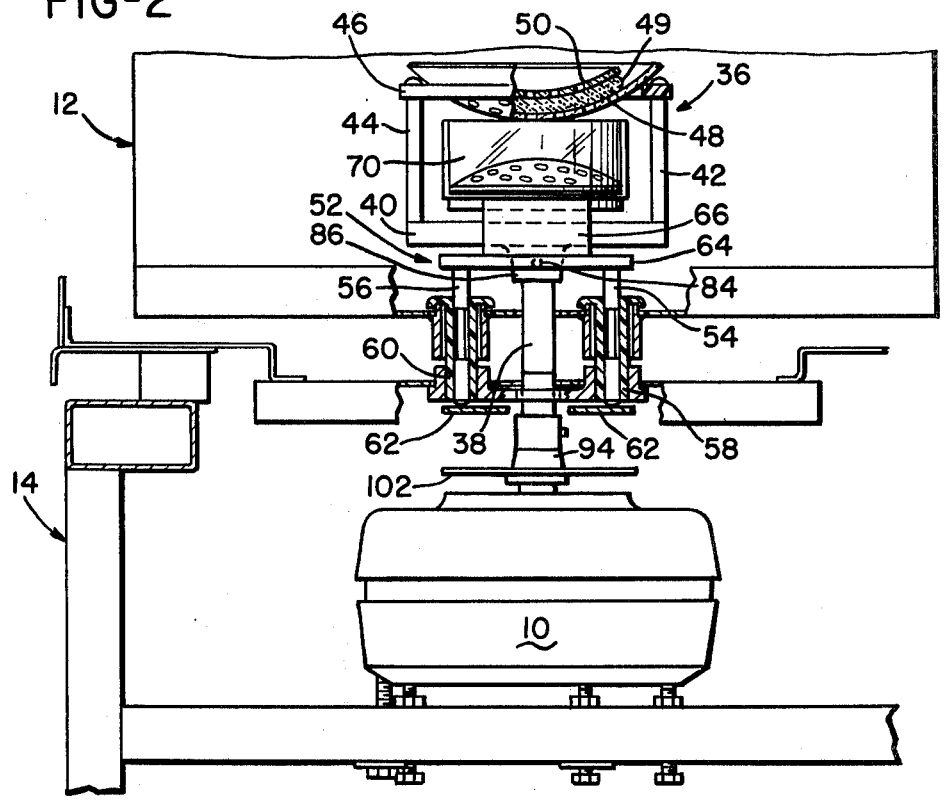
FIG. 2 is a view of the weighing apparatus, sample holder assembly, and fat collecting dish and dish support assembly in their respective positions during the cooking of the sample.

Referring now to FIGS. 1 and 2, this automated system includes a weighing balance assembly 10 incorporated beneath a microwave oven 12 which is supported on a suitable cabinet 14. The oven is a standard type of microwave oven using a magnetron with a frequency of 2450 megahertz, although frequencies of between 900 to 2500 megahertz may be used. This oven may be basically the same as a Model M312 microwave oven commercially available from the Hobart Corporation.

Oven 12 includes a hinged door 16. Below the oven on cabinet 14 is a control panel 20 which includes a master power (ON-OFF) switch 22 as well as the following controls. RESET switch 24 interrupts the program and returns control to the start of the program. CLEAR switch 26 clears any digits displayed in a window 28. CONT switch 30 when touched indicates that a command has been completed and continues the program to the next command. By touching switches NO 32 or YES 34 an operator can answer questions displayed in window 28. Finally, numbers entered into the program by touching digit switches 0-9 will be displayed in the window 28. A printer 23 records and displays information on a paper ticket.

Figure 5:
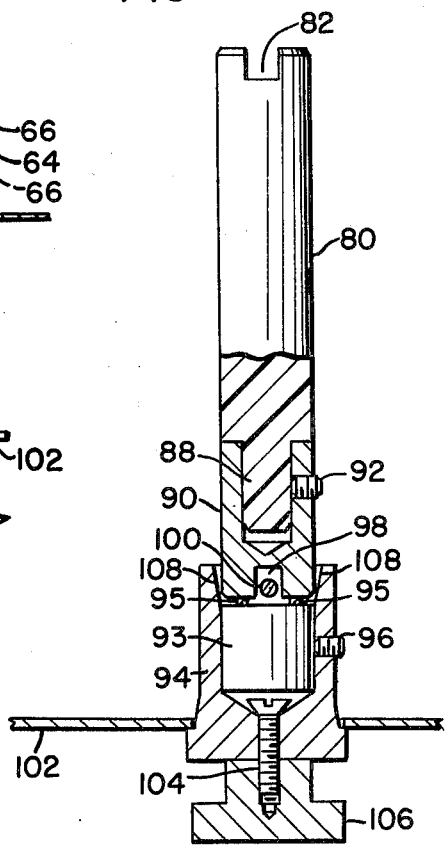
FIG. 5 is a detailed sectional view of the magnetic coupling of the stem of the weighing balance to the base thereof.

The weighing balance assembly 10 includes a precision balance such as a modified Model 5300 top loading balance commercially available from the Voland Corporation of New Rochelle, N.Y., having a sample holder assembly 36 mounted within the oven cavity on the pedestal stem 38 of the balance. As best illustrated in FIG. 5, the upper portion 80 of stem 38 is fabricated of a plastic, such as polypropylene, or other material substantially unaffected by microwave energy. At the upper tip of stem 38 is a slot 82 which is adapted to straddle pin 84 in boss 86 (illustrated in FIGS. 2 and 3) to provide proper alignment of the sample holder assembly 36 in the system.

The opposite tip 88 of upper portion 80 of the stem is adapted to fit into a hole bored in lower portion 90 of stem 38 and is held therein by suitable means such as set screw 92. Lower portion 90 of stem 38 is fabricated of a ferromagnetic material and is magnetically coupled to magnet 93 having poles 95 and seated in holder 94. A suitable magnet for use in the device has been found to be a BM-1908×⅜ magnet commercially available from Bunting Magnetics Co., Elk Grove Village, Ill. The magnet is held in place by suitable means such as a set screw 96. Stem 38 is maintained in proper alignment in holder 94 by means of slot 98 which straddles pin 100. A disc-like shield 102 protects the weighing mechanism from any possible fat drippings which may inadvertently escape from the oven. Holder 94 is secured by suitable means such as screw 104 to the balance mechanism 106.

As shown in FIG. 5, the upper portion 108 of the inner wall of holder 94 flares outwardly at an angle of about 7.5° from vertical to permit stem 38 to rock slightly away from the vertical while in the holder. The vertical movement of the stem is limited by the clearance between the stem and a ¼ wavelength choke seal which substantially eliminates any leakage of microwave energy from the opening in the oven bottom wall. Typically, this clearance is about ¼ inch. Thus, the magnetic coupling normally maintains the stem in a desired vertical position while still permitting a slight rocking motion of the stem relative to the magnet. This rocking motion, without magnetically uncoupling the stem, avoids the problem of transmitting possibly damaging forces or torques to the internal mechanism of the weighing device. The attraction between the magnet and the metallic lower portion of the stem insures that the stem will return to vertical once any external forces such as bumping or jarring have been removed from the stem and sample holder assembly.

Although a weighing balance having the weighing platform separated from the body portion by an elongated single shaft force transmitting element as does the Voland device is preferable for the present apparatus, it is possible to employ other forms of weighing apparatus including balances of the type wherein the force transducer is located inside the microwave oven cavity and only electrical wires are conducted to the cavity exterior if suitable changes are made in the apparatus. Balances which are totally mounted in the oven cavity and conduct electrical signals to the exterior would for example require suitable shielding and filtering devices to protect the balance transducers from microwave heating and to prevent microwave radiation from being conducted to the exterior of the heating cavity by the balance signal wiring.

Sample holder assembly 36 includes a base member 40 having a suitable connecting means such as boss 86 and pin 84 for releasably attaching the assembly to stem 38 of the balance. Boss 86 consists of a hollow shaft which fits over stem 38 and contains an alignment pin 84 to properly align the assembly on the stem. A pair of upstanding end walls 42 and 44 support an annular disc 46 which is attached thereto. The opening in disc 46 is proportioned to receive a sample holder 48 which may be a perforated watchglass. As illustrated in FIG. 2, a sample 49 of prepared meat is placed on sample holder 48 and is then covered by a sample holder cover 50. Preferably, sample holder cover 50 is also perforated to permit the escape of moisture from the sample as vapor during the cooking cycle. Both holder 48 and cover 50 may be formed of Pyrex glass or polytetrafluoroethylene (Teflon, a trademark of the duPont Company) or other suitable material which is nonresponsive (i.e., not heated) or only mildly responsive to microwave electromagnetic energy.

Also associated with weighing balance assembly 10 is a dish support assembly generally indicated at 52. This assembly includes a pair of vertically extending shafts 54 and 56 which extend through bushings 58 and 60, respectively, and rest on platform 62. Bushings 58 and 60 extend through the base of oven 12 into cabinet 14 and are sealed in the same manner as stem 38 to prevent leakage of microwave energy from the oven during operation. An annular disc-shaped support element 64 is attached to shafts 54 and 56 and surrounds stem 38. It has mounted on opposite sides thereof, a pair of upstanding members 66 and 68 which are adapted to support a dish 70.

Figure 4:
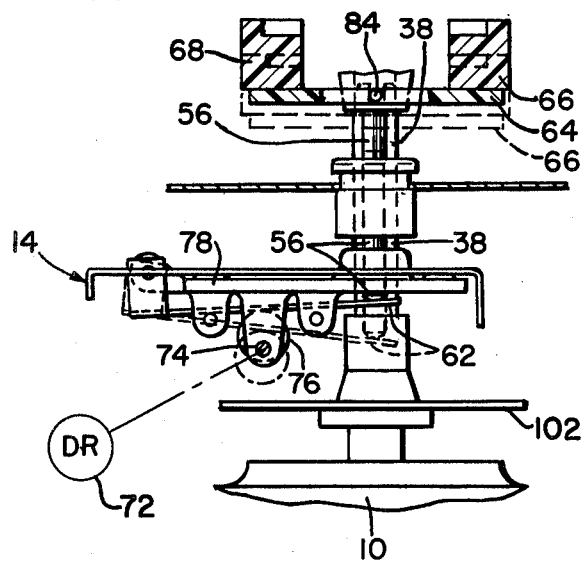
FIG. 4 is a side view of the mechanism which raises and lowers the dish support assembly.

Dish support assembly 52 is raised or lowered by raising or lowering platform 62. As best shown in FIG. 4, this is accomplished by a drive means 72 suitably connected to a shaft 74 which turns cam 76. Cam 76 is in direct contact with the underside of platform 62. Rotation of cam 76 causes platform 62, which is hinged at one end to support member 78 which is attached to a portion of cabinet 14, to raise and lower shafts 54 and 56. A limit switch (not shown) cuts off drive means 72 when the upper or lower (shown in dashed lines in FIG. 4) limit of platform movement is achieved.

Figure 3:
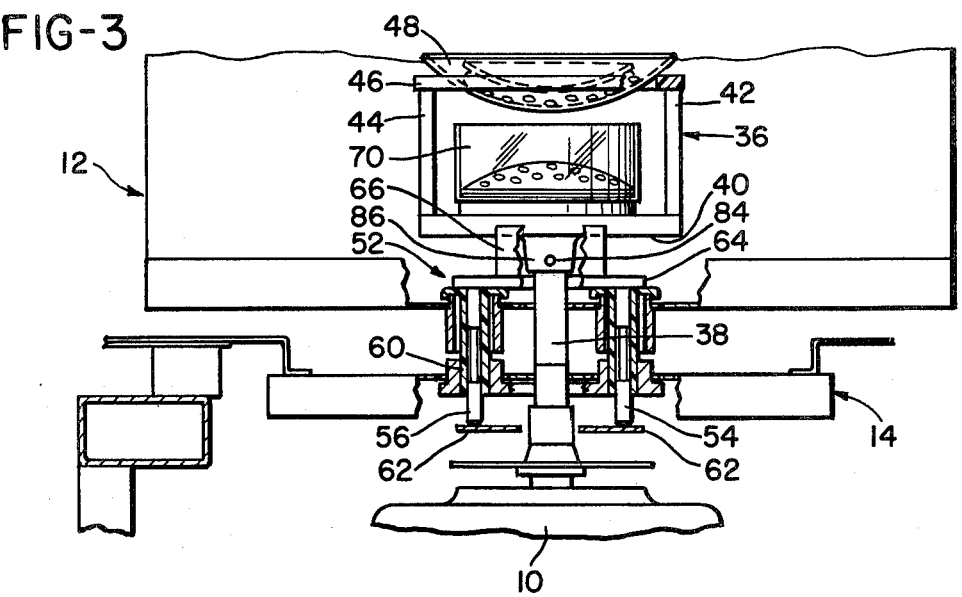
FIG. 3 is a view of the portion of the apparatus shown in FIG. 2, with the various elements shown in their respective positions after cooking has been terminated.

In this manner, dish 70 is raised off to sample holder assembly 36, as shown in FIG. 2, during the cooking cycle. Fat rendered from the sample during cooking is collected in dish 70 off of the weighing scale, avoiding erratic fluctuations in weight readings caused by explosions and spattering or dripping of the hot fat in the dish. After the cooking cycle has been terminated, dish 70 is lowered onto sample holder assembly 36 as shown in FIG. 3 where it is weighed.

The weighing balance device includes a digital electronic output and a microprocessor-controller as taught in the above-mentioned U.S. Pat. Nos. 3,890,825 and 3,916,670. The microprocessor-controller properly sequences the operation of the device and provides outputs to the display window 28 and printer 23. The operation of the microprocessor-controller is detailed in the above-mentioned patents and is herein incorporated by reference.

To commence operation for fresh meat analysis, the power is turned on by pressing ON switch 22. Then, the date, run number, meat type code, and temperature of the prepared sample are successively entered by the operator alternatively touching the appropriate digit switches and then the CONT switch 30 on the control panel. The microprocessor is programmed to utilize different predetermined values of slopes and intercepts in calculating the final percentages of fat, moisture, and protein in the sample. By entering the coded meat type (i.e., beef=0, pork=1, etc.) the microprocessor utilizes proper values for that particular type of meat for the calculations.

After this preliminary information has been entered, the command "PREPARE OVEN" is displayed in window 28. Then, the operator opens the oven door 16 and loads the sample holder assembly 36 including the sample holder 48 and sample cover 50 onto the weighing balance. At this time, also, collection dish 70 is loaded onto dish support assembly 52 which is in a raised position. After the operator closes the door 16 and touches CONT switch 30, a first tare weight (denoted SPT) of the sample support assembly, holder, and cover is taken and stored. The dish support assembly is then lowered causing dish 70 to be deposited onto the base member 40 of the sample holder assembly and a second tare weight (denoted S&D) which includes the weight of the collection dish is taken and stored. The microprocessor makes a calculation to confirm that the weight value of the collection dish (denoted as DSH) is within predetermined expected limits and that the operator has placed the dish on the dish support assembly. (The weight value DSH is not saved by the microprocessor). When this check is completed, the microprocessor causes the dish support assembly 52 to be raised so that the dish 70 is off of the sample holder assembly base member 40. Each actuation of the dish support assembly 52 to raise or lower the dish 70 is controlled by the microprocessor through its selective operation of the drive means 72 in a conventional manner.

Once the tare weights are recorded, the dish weight check performed, and the dish 70 raised off the weighing assembly 10, the microprocessor then displays a "LOAD SAMPLE" command on display window 28. Then, the operator loads a prepared sample between sample holder 48 and sample cover 50. Samples of fresh meat are prepared by grinding a sample through a conventional meat grinder and then mixing it to obtain a uniform composition. For best results, both the amount of mixing and temperature of the sample are controlled to enable accurate calibration of the analyzer and accurate sample analysis. It has been found that mixing for about 30 seconds at from 30°–50° F. produces satisfactory results.

After the operator closes the oven door 16 and touches the CONT switch 30, the microprocessor then performs a check to ascertain that the sample weight is within the desired range, for example 70 to 80 grams. First, the weight of the sample and sample holder assembly (denoted SAM and SPT) are taken and the initial sample weight calculation, SAM=(SAM+SPT)−SPT, is performed. If the sample weight should be above or below the desired range, the weight is displayed to the operator with the message "RELOAD". The operator is then required to adjust the sample weight to the proper range and again touch the CONT switch 30 to initiate the checking procedure. Once the sample weight is found to be within the proper range, the calculated weight value for the sample (SAM) is stored.

The operation for the analysis of a salted meat sample differs slightly from fresh meat analysis operation. This is due to the fact that meat proteins, as with many food proteins, have the ability to bind or encapsulate fat in an emulsion. The addition of salt to meat blends in meat processing operations aids in solubilizing the meat proteins and enables a greater amount of binding of fats. Likewise, temperature is an important factor in forming emulsions in a blended meat product, with higher temperatures (i.e., 50°–60° F.) producing more stable emulsions as opposed to lower temperatures (i.e., 30°–40° F.). Thus, varying the salt content, temperature, and amount of mixing of any meat blend varies the amount of fat bound in a meat sample of this blend and varies the resulting amount of fat rendered from a sample during heating. Accurate calibration becomes impossible for salted and blended samples which have undergone and indeterminate amount of mixing at an unknown temperature in the processing operation and during sample preparation. Thus, all sample preparations for a finished sample should be carried out for a definite time (i.e., 30 seconds to 1 minute) and at a temperature between 30° and 50° F.

In order to standardize the fat binding characteristics of salted blended meat samples, acid is added to the samples in an amount sufficient to lower the pH of the sample below the isoelectric point of the protein in the meat. At a pH below the isoelectric point, meant proteins have much less binding effect on fat and moisture, and the effects of the addition of salt to the meat can be counteracted.

It has been found that the use of citric acid for this purpose produces satisfactory results from the standpoint of ease of handling and production of samples from which accurate calibration measurements can be taken, although other acids may be utilized. A preferred form of citric acid is an encapsulated citric acid product commercially available from Durkee Foods, Inc. under the name Durkote citric acid (SR) (small granular). For use in this invention, the encapsulated acid is packaged in the form of a pillow or capsule. The citric acid is encapsulated in a fatty material which melts at 145°–150° F. Thus, the citric acid product may be mixed with a meat sample and the desirable pH lowering effect of the acid taken advantage of during cooking of the sample. It has been found that the addition of about 3 grams of this acid product to a 70–80 gram sample of meat produces satisfactory results.

In operation, the appropriate meat type code (i.e., blend=2, blend with water=3) is entered and the microprocessor utilizes the proper calibrated constant values for the program commands and required calculations. In addition to entering the appropriate meat type code, run number, and sample temperature, the operator must input the percentage of salt (salt weight divided by meat weight) in the sample to be analyzed.

The operator then prepares the oven as described above. However, when the CONT switch 30 is touched, the display window 28 will indicate "PRE-LOAD SAMPLE" instead of "LOAD SAMPLE" as described above. As before, the operator places the prepared meat sample on the sample holder assembly and by touching the CONT switch causes the microprocessor to read the balance weight measurement, SAM+SPT, calculate the sample weight, SAM=(SAM+SPT)−SPT, and then check if the sample weight is within the required 70 to 80 gram range. If the sample is within the proper weight range, its weight value is stored and the display will change to indicate "LOAD SAMPLE & ACID". The operator responds by opening the oven door and removing the sample to a mixing bowl. The contents of an acid pillow is added to the meat sample and mixed. The acid pillow preferably contains citric acid which acts to aid in the release of fat and moisture during the subsequent cooking of the sample. After the acid is mixed with the meat sample, the sample is then placed between the sample holder 48 and cover 50 and all are loaded on the sample holder assembly 36. The door is closed and the CONT switch 30 touched.

The microprocessor then reads the combined balance weight measurement of the sample, sample holder assembly, and acid (denoted as SAM+SPT+ACD) and calculates the weight of the sample and acid, SAM+ACD=(SAM+SPT+ACD)−SPT. Following that step, the weight of the acid is calculated (ACD=(SAM+ACD)−SAM) and a comparison is made to determine if the value ACD is greater than 1 gram. If it is greater, then the value SAM+ACD is substituted in storage for the value SAM and will thus replace SAM in calculation of subsequent values by the microprocessor.

The remainder of the analysis process is followed for all meat type codes. The microprocessor now turns on the power to oven 12 and cooking of the sample is commenced. The command "IN PROCESS" is displayed in window 28 during cooking. The microprocessor continuously monitors the change in weight of the sample during cooking until the time rate of change of weight loss is less than a predetermined value. A technique for accurate determination of oven turn-off is taught in U.S. Pat. Nos. 3,890,825 and 3,916,670 incorporated herein by reference. Procedures analogous to those taught in these patents are also utilized in the present system.

However, the above-described process and apparatus improve upon the methods taught in the above patents to achieve even more accurate determinations. Because the rendered fat is collected in dish 70 which in raised off of weighing balance 10, erratic fluctuations in weight readings caused by spattering or dripping and explosions in the collected fat are avoided. Since the weight loss being monitored is the sum of vaporized moisture and rendered fat, larger values are being measured with less chance of erroneous readings. The addition of acid to salted and/or blended meat samples standardizes their characteristics for purposes of accurate sample calibration. Moreover, the use of a magnetic coupling of the stem and sample holder assembly to the weighing balance mechanism avoids possibly damaging forces and torques being transmitted to the balance.

Once it has been ascertained by the microprocessor that the rate of sample weight decrease has declined to less than a predetermined value, the oven is turned off. After turn-off, dish 70 is lowered onto sample holder assembly 36 by activation of drive means 72. The total sample weight (denoted CTF) including the weight of the sample residue, fat, sample holder, sample holder cover, and holder assembly is then measured after a 10 second delay. This delay provides for the lapse of a period of time sufficient for spattering (or dripping) and explosions of rendered fat in the dish to have substantially subsided by the time the weight measurement is taken. After this delay, the microprocessor causes the caption "REMOVE RESIDUE" to be displayed. The operator then opens the oven door 16, removes the residue from the sample holder assembly, closes the door, and touches CONT switch 30 to cause the weight (denoted FNL) of the rendered fat, cover, holder, and holder assembly to be measured and stored. The microprocessor then automatically raises dish support assembly 52 with dish 70 off of the weighing balance in preparation for the next sample analysis.

Using the measured and stored weights, stored constants, derived weights, and the equations as defined below, the microprocessor can then calculate the percentages of fat, moisture, and protein in the sample. These final percentages (TPF, TPM, and TPP) are then displayed on window 28 and printed out by the printer 23 for a permanent record of the sample.

DEFINITIONS

SPT = Weight of sample holder and cover and sample holder assembly.
S&D = SPT plus weight of collection dish.
DSH = S&D − SPT, weight of collection dish including watchglass and paper.
SAM = Initial weight of sample.
ACD = Weight of acid.
CTF = Weight at cut-off of cooking of sample residue and rendered fat plus sample holder and cover, sample holder assembly, and collection dish.
FAT = Weight of rendered fat.
MST = Weight of vaporized moisture.
RES = Weight of sample residue.
FNL = Weight of rendered fat plus sample holder and cover, sample holder assembly, and collection dish.
RPF = Raw percent fat or fat percent by weight.
RPM = Raw percent moisture or moisture percent by weight.
TPF = True percent fat—correlated value.
TPM = True percent moisture—correlated value.
TPP = True percent protein—correlated value.

EQUATIONS

DSH = S&D − SPT
SAM = (SAM + SPT) − SPT
SAM & ACD = (SAM + SPT + ACD) − SPT
ACD = (SAM + ACD) − SAM
CTF = S&D + SAM − MST
FNL = S&D + FAT
FAT = FNL − S&D
MST = S&D + SAM − CTF
RPF = FAT/SAM
RPM = MST/SAM
$TPF = K_0 \pm K_1(RPF) \pm K_2(RPM) \pm K_3(TEMP) \pm K_4(SALT)$
$TPM = K_0 \pm K_1(RPF) \pm K_2(RPM) \pm K_3(TEMP) \pm K_4(SALT)$
$TPP = K_{1p} - K_{2p}(TPF) - TPM - SALT \%$

While the methods and apparatus described herein constitute preferred embodiments of the invention, it is to be understood that the invention is not limited to these precise methods and apparatus, and that changes may be made without departing from the scope of the invention, which is defined in the appended claims.

What is claimed is:

1. In a method of controlling the duration of application of microwave heating energy to a sample of food material containing fat which is heat releasable in liquid form in order to obtain a relatively constant chemical analysis of the residue of said sample, said method including the steps of (a) locating said sample on a weighing device, (b) applying energy to said sample to heat the same and cause fat in said sample to be rendered as a liquid, and (c) monitoring the weight of said sample during the applying of said energy thereto at least from a time when said sample begins losing weight, the improvement comprising:

collecting said fat rendered from said sample as liquid in a container which is moved relative to said weighing device so that it is off said weighing device during the applying of said energy to said sample and said monitoring of said weight loss of said sample, whereby erratic fluctuations in weight readings, which would otherwise be caused by spattering and explosions of the rendered fat if the fat were collected on the weighing device, are avoided.

2. In a method of controlling the duration of application of microwave heating energy to a sample of food material containing moisture and fat which are heat releasable respectively in vapor and liquid form in order to obtain a relatively constant chemical analysis of the residue of said sample, said method including the steps of (a) locating said sample on a weighing device, (b) applying energy to said sample to heat the same and cause moisture in said sample to be released as a vapor and fat in said sample to be rendered as a liquid, (c) monitoring the weight of said sample during the applying of energy thereto at least from a time when said sample begins losing weight, and (d) terminating the applying of energy to said sample when the time rate of change of the weight of said sample reaches a predetermined rate, the improvement comprising:

collecting said fat rendered from said sample as liquid in a container which is moved relative to said weighing device so that it is off said weighing device during the applying of said energy to said sample and monitoring of the weight loss of said sample whereby the weight loss being monitored is attributable both to vaporization of moisture and rendering of fat from said sample and thereby enhances the reliability of accurately determining when the predetermined time rate of change in weight loss of said sample occurs.

3. In a method of determining the amount of fat in a sample of food material wherein the fat is heat releasable in liquid form from said sample, said method including the steps of (a) applying microwave energy to said sample to heat the same and cause fat in said sample to be rendered as a liquid, (b) continuously monitoring the weight of said sample during the applying of energy thereto at least from a time when said sample begins losing weight, and (c) terminating the applying of energy to said sample once the residue of said sample reaches a predetermined chemical consistency, the improvement comprising:
(1) preparatory to applying energy to said sample,
  (i) mounting said sample on a holder assembly being, in turn, mounted on a weighing device;
  (ii) mounting a fat collecting receptacle on a support assembly being, in turn, mounted independent from said weighing device;
  (iii) moving said support assembly and said holder assembly relative to one another so as to locate said receptacle off said holder assembly and on said support assembly but in close proximity to said sample for receiving liquid fat rendered from said sample during subsequent applying of energy to said sample; and
(2) following the termination of application of energy to said sample, moving said support assembly and said holder assembly relative to one another so as to locate said receptacle off said support assembly and on said holder assembly for subsequent weighing of the rendered fat,
whereby spattering and explosions of rendered fat which occur in said receptacle during applying of energy to said sample will not be transmitted to said weighing device so as to interfere with the concurrent monitoring of the weight loss of said sample.

4. The method of claim 3 wherein said support assembly is moved upwardly relative to said holder assembly so as to lift said receptacle and locate the same off said holder assembly during application of energy.

5. The method of claim 3 wherein said support assembly is moved downwardly relative to said holder assembly so as to lower said receptacle and locate the same on said holder assembly and off said support assembly during weighing.

6. The method of claim 3 wherein said support assembly and said holder assembly are moved relative to one another to locate said receptacle off said support assembly and on said holder assembly only after a predetermined period of time has lapsed from termination of applying energy to said sample, said period of time being sufficient for spattering and explosions of rendered fat to have substantially subsided so as not to interfere with the subsequent weighing of the rendered fat.

7. In a method of determining the amount of fat in a meat product sample, said method including the steps of (a) locating said sample of meat on a weighing balance, (b) weighing said sample, (c) applying microwave energy to said sample to heat the same and cause fat in said sample to be released as a liquid, (d) continuously monitoring the weight of said sample during the applying of energy thereto at least from a time when said sample begins losing weight, and (e) terminating the applying of energy to said sample when the time rate of change of the weight of said sample reaches a predetermined rate, the improvement comprising:
collecting said fat rendered as a liquid in a container which is moved relative to said weighing device to that it is off said weighing device during said applying of energy to said sample; and
after terminating said applying of energy to said sample, placing the collected fat on said weighing device and weighing the fat with the sample residue.

8. The method of claim 7 wherein said collected fat is placed on said weighing device only after a predetermined period of time has lapsed from terminating said applying of energy to said sample, said period of time being sufficient for spattering and explosions of rendered fat to have substantially subsided so as not to interfere with the weighing of said fat with the sample residue.

9. In an apparatus for controlling the duration of application of microwave heating energy to a sample of food material containing fat which is heat releasable in liquid form in order to obtain a relatively constant chemical analysis of residue of said sample, said apparatus including a weighing device, means for locating said sample on said weighing device, means for applying energy to said sample to heat the same and cause fat in said sample to be rendered as a liquid, and means for monitoring the weight of said sample during the applying of energy thereto at least from a time when said sample begins losing weight, the improvement comprising:
container means for collecting the fat rendered from said sample as liquid and means to move said container means relative to said weighing device so that it is off said weighing device during the applying of said energy to said sample by said energy applying means and the monitoring of said weight loss of same sample by said monitoring means, whereby erratic fluctuations in weight readings, which would otherwise be caused by spattering and explosions of the rendered fat if the fat were collected on the weighing device, are avoided.

10. In an apparatus for controlling the duration of application of microwave heating energy to a sample of food material containing moisture and fat which are heat releasable respectively in vapor and liquid form in order to obtain a relatively constant chemical analysis of the residue of said sample, said apparatus including a weighing device, means for locating said sample on said weighing device, means for applying energy to said sample to heat the same and cause moisture in said sample to be released as a vapor and fat in said sample to be rendered as a liquid, and means for monitoring the weight of said sample during the applying of energy thereto at least from a time when said sample begins losing weight and for terminating the applying of energy to said sample when the time rate of change of the weight of said sample reaches a predetermined rate, the improvement comprising:
container means for collecting the fat rendered from said sample as liquid and means to move said container means relative to said weighing device so that it is off said weighing device during the applying of energy to said sample by said energy applying means and the monitoring of the weight loss of said sample by said monitoring means, whereby the weight loss being monitored is attributable both to vaporization of moisture and rendering of fat from said sample and thereby enhances the reliability of accurately determining when the predetermined time rate of change in weight loss of said sample occurs.

11. In an apparatus for determining the amount of fat in a sample of food material wherein the fat is heat releasable in liquid form from said sample, said apparatus including a sample holder assembly for supporting said sample, heating means having an enclosure for receiving said sample holder assembly and applying microwave energy to said sample supported by said assembly to heat said sample and cause fat in said sample to be rendered as liquid, a receptacle for collecting the fat rendered from said sample, weighing means connected to said sample holder assembly and supporting the same within said enclosure for weighing the same together with anything placed thereon and providing an output related to said weighing, and computing means connected to receive said output of said weighing means and calculate therefrom the amount of fat in said sample, the improvement comprising:
- a receptacle support assembly mounted in said apparatus independent from said weighing means and said sample holder assembly; and
- means for moving said receptacle support assembly and said sample holder assembly relative to one another so as to locate said receptacle off said holder assembly and on said support assembly but in close proximity to said sample for receiving liquid fat rendered from said sample during the application of energy to said sample,
- whereby spattering and explosions of rendered fat which occur in said receptacle during application of energy to said sample and when said receptacle is located off said sample holder assembly will not be transmitted to said weighing means which is connected to said sample holder assembly so as to interfere with said weighing by said weighing means.

12. The apparatus of claim 11, in which said sample holder assembly includes a base member, a pair of upstanding members at either end of said base member, an annular disc spanning said upstanding members, and a perforated dish held in said annular disc for containing the sample to be analyzed.

13. The apparatus of claim 11 in which said receptacle support assembly includes a pair of vertically extending shafts, an annular disc member spanning the top of said shafts, and a pair of upstanding side members on opposite sides of said disc, said shafts capable of being raised and lowered by said means for moving said receptacle support assembly for causing said side members to engage said receptacle and raise and lower it off and onto said base member of said sample holder assembly.

* * * * *